United States Patent
Hill

(10) Patent No.: US 10,085,393 B2
(45) Date of Patent: Oct. 2, 2018

(54) LONG RANGE, BATTERY POWERED, WIRELESS ENVIRONMENTAL SENSOR INTERFACE DEVICES

(75) Inventor: Jason Lester Hill, Capistrano Beach, CA (US)

(73) Assignee: The Toro Company, Bloomington, MN (US)

( * ) Notice: Subject to any disclaimer, the term of this patent is extended or adjusted under 35 U.S.C. 154(b) by 2346 days.

(21) Appl. No.: 12/775,332

(22) Filed: May 6, 2010

(65) Prior Publication Data

US 2011/0273196 A1 Nov. 10, 2011
US 2013/0099806 A9 Apr. 25, 2013

Related U.S. Application Data

(63) Continuation of application No. 11/346,121, filed on Feb. 2, 2006, now Pat. No. 7,719,432.

(60) Provisional application No. 60/650,160, filed on Feb. 4, 2005.

(51) Int. Cl.
*A01G 25/16* (2006.01)
*H04Q 9/00* (2006.01)

(52) U.S. Cl.
CPC ............. *A01G 25/167* (2013.01); *H04Q 9/00* (2013.01); *H04Q 2209/25* (2013.01); *H04Q 2209/40* (2013.01); *H04Q 2209/886* (2013.01)

(58) Field of Classification Search
CPC .... A01G 25/167; A01G 25/16; G01N 33/246; G01N 27/048; G01N 22/04; G01N 33/24; H04W 4/00; Y10T 137/189
USPC ............. 73/73; 324/658, 663, 664, 686, 689
See application file for complete search history.

(56) References Cited

U.S. PATENT DOCUMENTS

| | | | | |
|---|---|---|---|---|
| 2,793,527 A | * | 5/1957 | Turner, Jr. | G01N 27/121 324/448 |
| 3,114,243 A | * | 12/1963 | Winters | 405/37 |
| 3,783,804 A | | 1/1974 | Platz | |
| 3,794,992 A | | 2/1974 | Gehman | |
| 3,905,551 A | * | 9/1975 | Ayme de la Chevreliere | 239/63 |

(Continued)

FOREIGN PATENT DOCUMENTS

GB 2247951 A 3/1992
WO WO 2004068436 A1 * 8/2004 ............. G08C 17/00

OTHER PUBLICATIONS

"Hydra Soil Moisture Probe User's Manual", Stevens Vitel, Inc., Jun. 1994.*

(Continued)

*Primary Examiner* — David A Rogers
(74) *Attorney, Agent, or Firm* — Inskeep IP Group, Inc.

(57) ABSTRACT

Long range, battery powered, wireless environmental sensor interface devices that can be connected to a plurality of sensors and wirelessly communicate the sensor readings back to a central collection device or Internet terminal. Instead or additionally, sensors can be integrated with the device for added efficiency. The devices incorporate a rugged enclosure and an internal power supply that allows them to be placed in harsh environmental conditions and operate for multiple years without maintenance due to unique power-saving design features. The RF circuitry is specially optimized for long-range outdoor communications of small quantities of data. Line-of-sight communication range of several miles is possible with this device. Various embodiments are disclosed.

20 Claims, 4 Drawing Sheets

(56) References Cited

U.S. PATENT DOCUMENTS

| | | | |
|---|---|---|---|
| 4,184,789 A | | 1/1980 | Gilde, Jr. |
| 4,445,788 A | | 5/1984 | Twersky et al. |
| 4,455,631 A | | 6/1984 | San Giovanni |
| 4,567,563 A | | 1/1986 | Hirsch |
| 4,693,419 A | * | 9/1987 | Weintraub et al. ............ 239/63 |
| 4,726,239 A | | 2/1988 | Boggess et al. |
| 4,801,865 A | * | 1/1989 | Miller et al. .................. 324/696 |
| 4,814,608 A | | 3/1989 | Dempsey et al. |
| 4,847,781 A | | 7/1989 | Brown, III et al. |
| 4,852,802 A | | 8/1989 | Iggulden et al. |
| 4,886,088 A | * | 12/1989 | Ryokai et al. ............... 137/78.3 |
| 5,150,622 A | | 9/1992 | Vollweiler |
| 5,179,347 A | | 1/1993 | Hawkins |
| 5,209,129 A | | 5/1993 | Jaselskis et al. |
| 5,385,297 A | | 1/1995 | Rein et al. |
| 5,418,466 A | | 5/1995 | Watson et al. |
| 5,424,649 A | * | 6/1995 | Gluck et al. .................. 324/667 |
| 5,570,030 A | * | 10/1996 | Wightman .................... 324/694 |
| 5,621,669 A | | 4/1997 | Bjornsson |
| 5,635,710 A | | 6/1997 | Reed et al. |
| 5,646,537 A | * | 7/1997 | Skaling et al. ............... 324/643 |
| 5,714,931 A | | 2/1998 | Petite et al. |
| 5,740,031 A | | 4/1998 | Gagnon |
| 5,765,304 A | * | 6/1998 | Clark .......................... 47/58.1 R |
| 5,813,606 A | * | 9/1998 | Ziff ...................... A01G 25/167 |
| | | | 239/63 |
| 5,825,295 A | * | 10/1998 | Casady et al. ................ 340/602 |
| 5,898,310 A | * | 4/1999 | Liu ............................... 324/690 |
| 5,926,103 A | | 7/1999 | Petite |
| 5,926,531 A | | 7/1999 | Petite |
| 6,014,029 A | * | 1/2000 | Soto et al. .................... 324/664 |
| 6,028,522 A | | 2/2000 | Petite |
| 6,044,062 A | | 3/2000 | Brownrigg et al. |
| 6,082,816 A | | 7/2000 | Gottlieb et al. |
| 6,202,479 B1 | * | 3/2001 | Frybarger .......................... 73/73 |
| 6,215,317 B1 | * | 4/2001 | Siddiqui et al. ............. 324/643 |
| 6,218,953 B1 | | 4/2001 | Petite |
| 6,233,327 B1 | | 5/2001 | Petite |
| 6,249,516 B1 | | 6/2001 | Brownrigg et al. |
| 6,275,500 B1 | | 8/2001 | Callaway, Jr. et al. |
| 6,278,412 B1 | | 8/2001 | Kelly et al. |
| 6,430,268 B1 | | 8/2002 | Petite |
| 6,437,692 B1 | | 8/2002 | Petite et al. |
| 6,452,499 B1 | | 9/2002 | Runge et al. |
| 6,600,971 B1 | | 7/2003 | Smith et al. |
| 6,601,440 B1 | | 8/2003 | Chuang |
| 6,618,578 B1 | | 9/2003 | Petite |
| 6,628,764 B1 | | 9/2003 | Petite |
| 6,671,586 B2 | | 12/2003 | Davis et al. |
| 6,719,488 B2 | * | 4/2004 | Kuroda et al. ................. 405/36 |
| 6,747,557 B1 | | 6/2004 | Petite et al. |
| 6,784,807 B2 | | 8/2004 | Petite et al. |
| 6,836,737 B2 | | 12/2004 | Petite |
| 6,862,498 B2 | | 3/2005 | Davis et al. |
| 6,891,838 B1 | | 5/2005 | Petite et al. |
| 6,914,533 B2 | | 7/2005 | Petite |
| 6,914,893 B2 | | 7/2005 | Petite |
| 6,931,445 B2 | | 8/2005 | Davis |
| 6,975,236 B2 | | 12/2005 | Staples |
| 6,978,794 B2 | * | 12/2005 | Dukes et al. ..................... 137/1 |
| 7,019,667 B2 | | 3/2006 | Petite et al. |
| 7,053,767 B2 | | 5/2006 | Petite et al. |
| 7,054,271 B2 | | 5/2006 | Brownrigg et al. |
| 7,079,810 B2 | | 7/2006 | Petite et al. |
| 7,103,511 B2 | | 9/2006 | Petite |
| 7,114,376 B2 | * | 10/2006 | Loucks et al. .................... 73/73 |
| 7,114,388 B1 | | 10/2006 | French et al. |
| 7,137,550 B1 | | 11/2006 | Petite |
| 7,183,779 B2 | * | 2/2007 | Hughes ......................... 324/696 |
| 7,184,861 B2 | | 2/2007 | Petite |
| 7,187,299 B2 | * | 3/2007 | Kunerth et al. ......... 340/870.05 |
| 7,209,840 B2 | | 4/2007 | Petite et al. |
| 7,216,659 B2 | * | 5/2007 | Caamano et al. ................ 137/1 |
| 7,240,743 B2 | | 7/2007 | Buss et al. |
| 7,263,073 B2 | | 8/2007 | Petite et al. |
| 7,281,439 B2 | | 10/2007 | Schmitt et al. |
| 7,295,128 B2 | | 11/2007 | Petite |
| 7,788,970 B2 | * | 9/2010 | Hitt et al. .......................... 73/73 |
| 8,035,403 B1 | * | 10/2011 | Campbell et al. ............ 324/694 |
| 2001/0002210 A1 | | 5/2001 | Petite |
| 2002/0013679 A1 | | 1/2002 | Petite |
| 2002/0027504 A1 | | 3/2002 | Davis et al. |
| 2002/0028347 A1 | | 3/2002 | Marrocco, III et al. |
| 2002/0031101 A1 | | 3/2002 | Petite et al. |
| 2002/0060576 A1 | * | 5/2002 | Tominaga ............ G01N 27/048 |
| | | | 324/715 |
| 2002/0112531 A1 | | 8/2002 | Hubbell et al. |
| 2002/0144453 A1 | | 10/2002 | Su |
| 2002/0169643 A1 | | 11/2002 | Petite et al. |
| 2003/0024155 A1 | * | 2/2003 | Kuroda et al. ............. 47/1.01 R |
| 2003/0036810 A1 | | 2/2003 | Petite |
| 2003/0078029 A1 | | 4/2003 | Petite |
| 2003/0080199 A1 | * | 5/2003 | Condreva ........................ 239/63 |
| 2003/0230638 A1 | * | 12/2003 | Dukes et al. .................. 239/200 |
| 2004/0183687 A1 | | 9/2004 | Petite et al. |
| 2006/0022835 A1 | | 2/2006 | Rice |
| 2006/0139037 A1 | | 6/2006 | Hughes |
| 2006/0144437 A1 | * | 7/2006 | Dresselhaus et al. ....... 137/78.3 |
| 2006/0181406 A1 | | 8/2006 | Petite et al. |
| 2006/0202853 A1 | | 9/2006 | Davis et al. |
| 2007/0135973 A1 | | 6/2007 | Petite |
| 2007/0273394 A1 | | 11/2007 | Tanner et al. |

OTHER PUBLICATIONS

"Hydra Soil Moisture Probe and Hydra Logger", Stevens Vitel, Inc., retrived from the Internet Archive at <http://web.archive.org/web/20041028010729/http://www.stevenswater.com/soil_moisture_sensors/index.html>, archived on Oct. 28, 2004.*

Seyfried et al., "Measurement of Soil Water Content with a 50-MHz Soil Dielectric Sensor", Soil Science Society of America Journal, Mar.-Apr. 2004.*

"Mongolia Reference Site DGS Station", University Corporation for Atmospheric Research, Mar. 2003.*

M. A. Hilhorst, "A Pore Water Conductivity Sensor", Soil Science Society of America Journal, Nov.-Dec. 2000.*

Water Repellancy, Soil Physics and Land Use Group, available on the internet at http://www.splu.nl/waterrepellency/dut.htm, 2000.*

W.E.T Sensor, Delta-T Devices, Ltd., Oct. 18, 2002.*

Hill, Jason et al., "System Architecture Directions for Networked Sensors," ASPLOS-IX, Cambridge, Massachusetts, Nov. 2000.

Hill, Jason Lester, "System Architecture for Wireless Sensor Networks," Ph.D. Thesis published at the University of California at Berkeley, 2003, pp. 1-186.

Chakeres, Ian D. et al., "AODV Routing Protocol Implementation Design," Proceedings of the International workshop on Wireless Ad Hoc Networking (WWAN), Tokyo, Japan, Mar. 2004.

Culler, David et al., "Overview of Sensor Networks," IEEE Computer, Special Issue in Sensor Networks, Aug. 2004, pp. 41-49.

* cited by examiner

LONG RANGE, BATTERY POWERED, WIRELESS ENVIRONMENTAL SENSOR INTERFACE DEVICES

CROSS-REFERENCE TO RELATED APPLICATION

This application is a continuation of U.S. patent application Ser. No. 11/346,121, filed Feb. 2, 2006 (now U.S. Pat. No. 7,719,432 issued May 18, 2010), entitled *Long Range, Battery Powered, Wireless Environmental Sensor Interface Devices*, which in turn claims the benefit of U.S. Provisional Patent Application No. 60/650,160 filed Feb. 4, 2005, entitled Long Range, Battery Powered, Wireless Environmental Sensor Interface Devices, both of which are incorporated herein by reference in their entireties.

BACKGROUND OF THE INVENTION

1. Field of the Invention

The present invention relates generally to wireless sensing devices and sensor communication devices.

2. Prior Art

In many industrial fields, it is important to continually measure and monitor environmental parameters. In agricultural industries, it is essential to monitor water content of soil and concentration of fertilizers. In chemical industries it is essential to monitor the air for possible hydrocarbon or toxic gas leaks that could lead to industrial accidents. At airports it is important to monitor the integrity of fencing surrounding the property. All of these applications can greatly benefit from a self-contained wireless data transmitter specifically designed to interface with sensors.

All of these example applications have similar requirements: that the device be low cost, easy to install, resistant to the weather, have long battery life, and can communicate large distances in order to easily cover a large area.

In the prior art, there exist three distinct classes of environmental sensors. The first class is of low-cost battery powered devices that are designed to operate around a home or building. They often take the form of wireless smoke detectors, motion detectors or weather stations. These devices are single purpose and short-range. There is no option to connect any external sensors or customize the sensor pack. Additionally, their short range design does not allow them to be used in large-scale industrial settings or large outdoor settings.

The second class of devices is the wireless sensor transmitters most similar to the device described in this document. They are designed to interface to a handful of different sensors and transmit the data back to a display terminal. Many of them also log data internally. While their range is relatively limited, they can transmit the data up to several thousand feet. These devices, however, are both large and expensive. They generally mount on poles or tripods in order to elevate the antenna. While they include batteries for nighttime operation, they heavily rely on solar cells to supply them with power. The mounting requirements and solar cell requirements add significant cost to the devices that impact their usability and installation time.

The third class of wireless sensor interface devices is a group of stand-alone sensor and communication devices that use wide area wireless communication technologies. These devices connect to a sensor and then communicate sensor readings via cell phone, pager, or satellite phone communication systems. These devices are designed for use in remote areas. These devices also required an above ground mounting and rely heavily on solar cells as a power source. While useful, these devices require that the operator pay for access to the wireless network. Cellular and satellite communication charges can add up quickly when transmitting data every few minutes. To avoid excessively high charges these devices often collect data for several hours or days and then transmit the data in a batch. The devices described herein use unlicensed band communication frequencies and do not require the operator to pay for service or licensing fees.

DETAILED DESCRIPTION OF THE PREFERRED EMBODIMENTS

Figure 1:
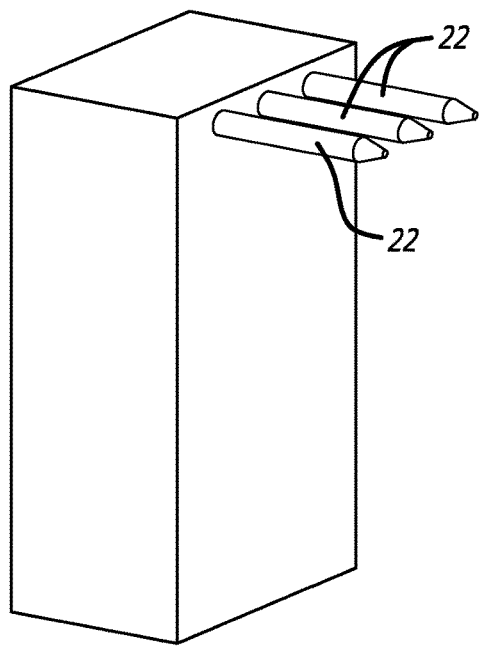
FIG. 1 is an illustration of one embodiment of the present invention.

The preferred embodiments of the present invention long range, battery powered, wireless environmental sensor interface devices described herein are small, self-contained and can be placed on or even under the ground. For example, soil moisture sensors can be installed in seconds by making a small hole in the ground, inserting the node, and covering it back up. This is in sharp contrast to the existing wireless sensor interface devices that require both the purchase and installation of a mounting pole and large solar cell. With the low power design described in this document, small internal batteries provide all the power necessary to operate for several years. While battery replacement is possible, the low-cost nature of the device makes it practical to simply throw it away when the batteries die. These differences place this design is a different class than that of existing devices.

In addition to communicating with base-station type receiver devices, the present invention described herein is also capable of exploiting Mesh networking techniques. As each device is capable of bi-directional communications, individual sensor devices can communicate with each other. By using multi-hop networking techniques, data from distant nodes can be relayed toward collection points by intermediate sensor nodes. In this type of network, each sensor node can act as both a sensor and as a data relay point.

More information on Mesh networking that can be applied for use in embodiments of the present invention can be found in:

"System Architecture Directions for Network Sensors", Jason Hill, Robert Szewczyk, Alec Woo, Seth Hollar, David Culler, Kristofer Pister, ASPLOS 2000, Cambridge, November 2000; and, "Overview of Sensor Networks", David Culler, Deborah Estrin, Mani Srivastava, IEEE Computer, Special Issue in Sensor Networks, August 2004; and, "Mica: A Wireless Platform for Deeply Embedded Networks", Jason Hill and David Culler, IEEE Micro., vol 22(6), November/December 2002, pp 12-24.

The disclosures of the foregoing references are hereby incorporated herein by reference.

The ability to exploit Mesh communication techniques provides a significant advantage over other technologies. Mesh techniques makes network communication significantly more reliable. Additionally, it allows for automatic configuration and reconfiguration to a dynamic environment. Node failure or movement can be handled automatically by autonomous reconfiguration of the Mesh network.

Thus the present invention relates to a device that can function as a member of a distributed set of environmental sensors and provide for the collection of data from them. The device can be connected to one or more environmental sensors and will wirelessly transmit the sensor data back to a collection device or Internet terminal for storage. Measuring just a few inches on a side, the device can be placed unobtrusively in the environment near the sensors.

The device has a sealed cavity that protects the communication electronics and battery source. One example of the device has a set of sensor interface wires emerging from the sealed cavity that can be connected to a plurality of sensors. Depending on range requirements an external antenna may also be used. For many applications an internal antenna will provide sufficient communication range. Use of an internal antenna will make the device more rugged. It is essential that all openings in the sealed cavity be weatherproof.

The preferred embodiments of the devices contain a 902-928 MHz narrow band, frequency hopping transceiver. This has been selected because it can be used highly efficiently for long-range communication. 900 MHz transmission propagates well in an outdoor environment. Additionally, FCC regulation allows the use of this band without licensing at transmission power up to 1 Watt. In some versions, the transmitter can transmit up to 1 Watt and uses frequency hopping to avoid interference.

In order to reduce the power consumption of the devices, precise time synchronization is used to allow the devices to remain powered off for long periods of time. After initial synchronization, a device will power itself off until data needs to be communicated. Through the use of time synchronization, the devices can power back on in sync with the receiver and transmit the data. This synchronization is maintained throughout the life of the devices. If synchronization is lost for any reason, a device can perform a resynchronization step as necessary. Generally, transmission is intermittent (short bursts), and the sensors will only be powered just before or during a transmission to greatly reduce sensor power requirements and provide a sample reading of the parameter being measured for communication.

Initial time synchronization is established when each device is powered on. During start-up, each device will transmit a time search message on sequential channels until it receives a reply. The reply message will inform the device of the current time and the current hopping channel. During operation, devices can transmit a time search message at any time and listen for a reply from surrounding nodes. Typically this is done on the current frequency hopping channel. However, it is also done on random hopping channels to check for alternate hop schedules. If an alternate hopping schedule is detected, the device can choose to switch to that schedule. This decision is generally made based on priority.

Figure 5:
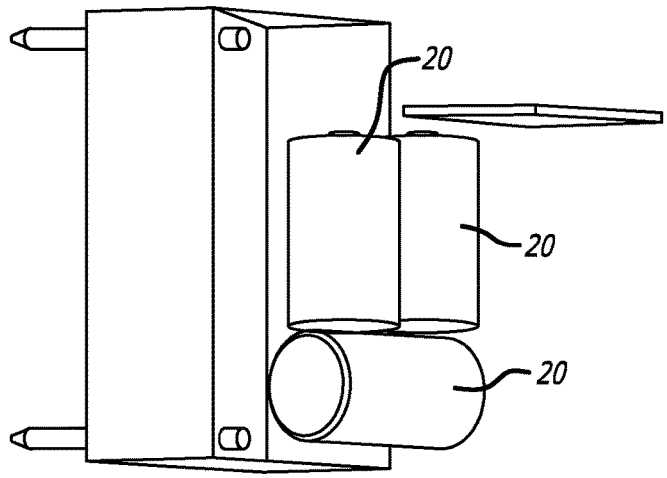
FIG. 5 is an exploded view of one embodiment of the present invention.
Figure 6:
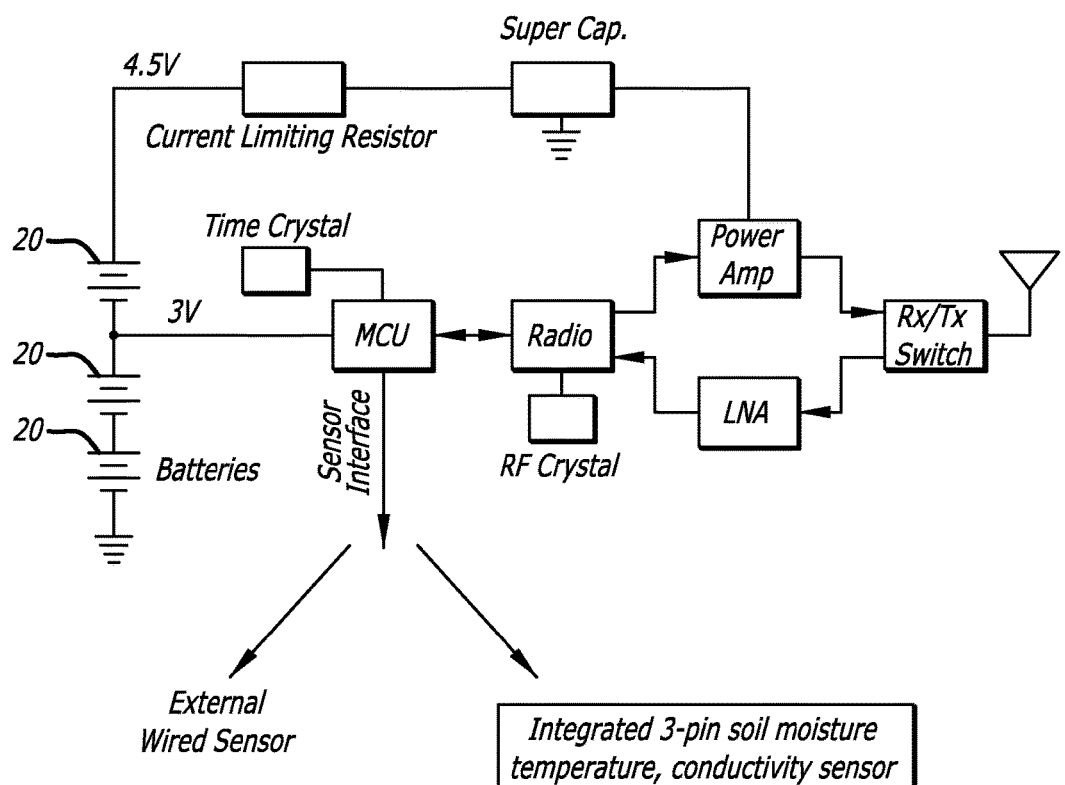
FIG. 6 is a block diagram of the circuitry of one embodiment of the present invention.

In one instance of the device, alkaline batteries are used. Alkaline batteries are selected because of their low cost and high energy density. One of the drawbacks of the alkaline batteries is that the voltage sags significantly as the battery discharges. To compensate for this, a preferred embodiment of the device uses a unique arrangement of three alkaline cells 20, as shown in the exploded view of FIG. 5 and the block diagram of FIG. 6. The three Alkaline cells are connected in series (FIG. 6). Power is extracted from the first two batteries in the series connection of the three batteries. This allows them to initially supply a 3V source for the microcontroller MCU and transceiver (Radio and RX/TX switch) and a 4.5V source for the transmitter Power Amplifier and low noise amplifier LNA. As the batteries discharge, they will droop to 2V and 3V respectively. By connecting the batteries in this fashion, the microcontroller MCU contained in the device and the low power receiver can operate in the 3V to 2V range while the RF Power Amplifier and front end LNA can operate in the 4.5V to 3V range. If only one 3V source were used, then the device performance would degrade significantly when the supply drooped past 2.7V. Alternatively, if a single 4.5 V source were used, then a regulator would have to be provided to supply a maximum of 3.3 V to the transceiver and microcontroller. The power consumption of the regulator alone would significantly impact the device lifetime.

In the preferred embodiment of the devices, in addition to the unique battery connection, the devices also contain a power supply filter (The Super Cap.) between the power amplifier and the rest of the system. The filter is designed to isolate the microcontroller MCU and transceiver from the power drain of the Power Amplifier. If the Power Amplifier were to be directly connected to the 4.5V tap on the alkaline power source, a significant voltage spike would appear at both the 4.5V and the 3V tap when the amplifier was turned on. This would introduce a noise spike into both the radio and the microcontroller. To prevent this, a Current Limiting Resistor is placed between the 4.5V tap and a large buffer capacitor Super Cap. In a preferred embodiment, a 2 Farad capacitor is used in conjunction with a 47 Ohm current limiting resistor. This resistor prevents the Power Amplifier from drawing more than a few milliamps directly from the alkaline batteries 20. A majority of the current to run the Power Amplifier in short bursts is provided by the Super Cap. By limiting the surge current from the batteries, the 3V battery tap remains stable throughout a transmission. Without the Current Limiting Resistor, a voltage drop of up to 0.5 volts can disrupt proper operation of the low voltage components.

In addition to being able to connect external sensors to this device, it is also possible to include internal sensors in the package. A preferred embodiment of the invention is a device with integrated sensors built in to the device. By default, the device includes a battery voltage sensor and a temperature sensor. It can be extended to include internal accelerometers or even soil moisture and salinity sensors (see FIG. 6).

One preferred embodiment of the device has been designed so that it has three external stainless steel pins 22 that extend from the package to interface with the soil in order to determine the soil moisture content, conductivity levels and temperature, as shown in FIG. 1. By properly exciting the pins, the microcontroller MCU can measure the conductivity of the soil between the pins and the capacitance of the soil. The three pins that extend from the device are arranged in a line. The outer two pins are connected to ground. The inner pin is excited with a voltage and the response of the pin is measured. A higher capacitance corresponds to higher moisture content in the soil. Higher conductivity corresponds to higher salt content in the soil. A thermistor (temperature sensitive resistor) is placed at the base of one of the pins in order to measure the temperature of the pin, and therefore the temperature of the soil. To achieve accurate measurements, the moisture, salinity and temperature measurements are cross compensated. Soil conductivity naturally increases as soil moisture increases even if the salt content has not increased. Cross compensation allows salt content to be accurately measured across a wide range of moisture levels. The device of FIG. 1 may instead or also include wires for connection to one or more external sensors.

In a preferred embodiment, a single microcontroller MCU coordinates exciting the sensor pin, measuring the response and orchestrating the RF communication protocols. This creates a device that is both low cost and highly efficient.

Figure 2:
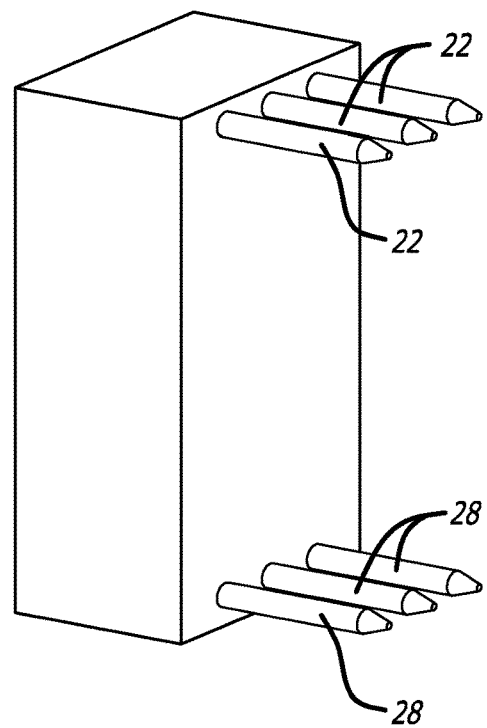
FIG. 2 is an illustration of another embodiment of the present invention.

In addition to sensing the soil moisture, temperature, and conductivity at a singe point, there is also a preferred embodiment that interfaces with the soil at multiple points. FIG. 2 shows a soil moisture sensor that interfaces with the soil at two depths using sensor pins 22 and 28.

Figure 3:
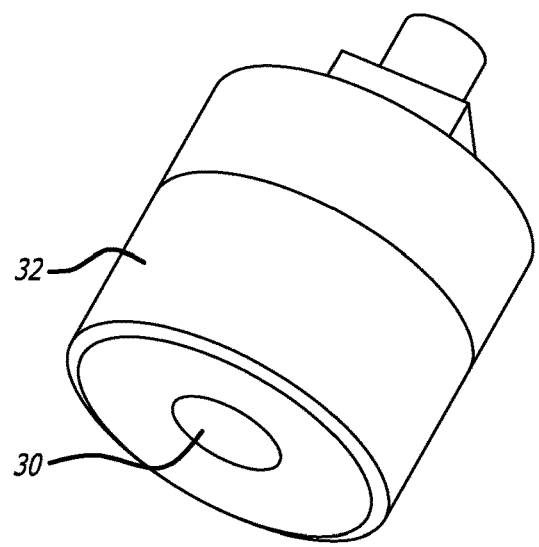
FIG. 3 is an illustration of still another embodiment of the present invention.

A version of the environmental sensor device has been designed that contains an ultrasonic ranging sensor for detecting and reporting liquid levels and/or distances to objects as shown in FIG. 3. The device can be placed at a fixed level above a holding tank and measure the distance down to the liquid inside. This can be used to monitor water levels in lakes and reservoirs. The microcontroller MCU excites the ultrasonic transducer 30 and measures the response in order to determine the range to the nearest object, and then communicates the result over the RF transceiver. In this design, the electronics are housed in a circular package 32 with an ultrasonic sensor 30 exposed at the bottom as shown in FIG. 3.

For external sensors, the external sensor interface is designed so a wide array of sensors can be connected. This includes analog interfaces, resistive interfaces and digital interfaces. Examples of each include analog accelerometers, resistive thermistors and digital soil moisture sensors. The resistive interface compares the external resistance to a set of internal known resistances. The device is able to auto-scale for external resistance ranging from mega-ohms to ohms.

Figure 4:
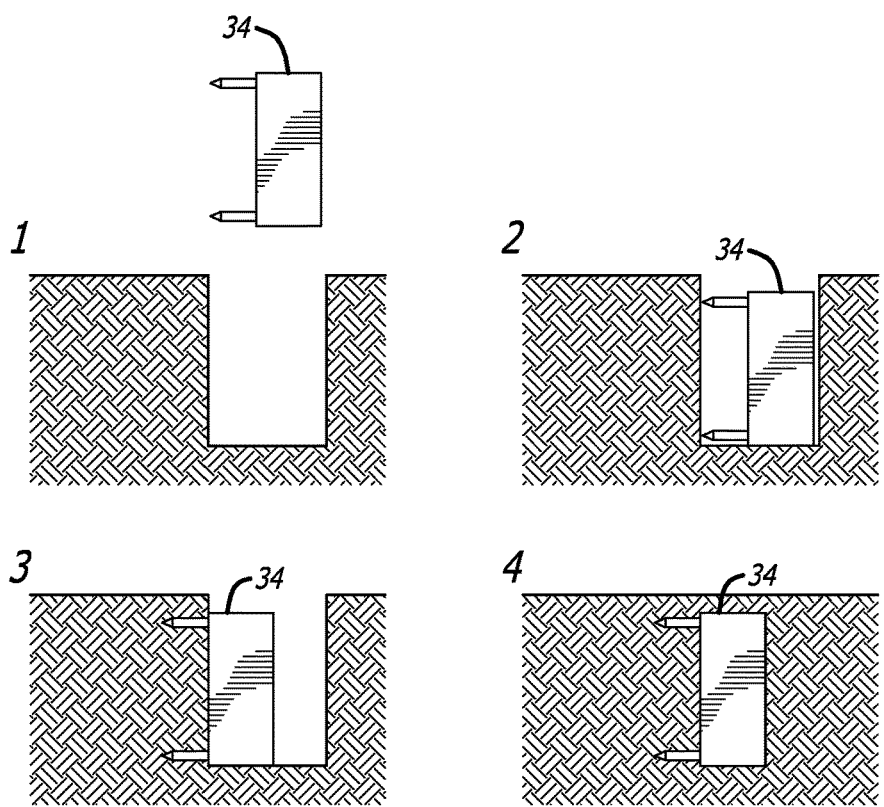
FIG. 4 is an illustration of the insertion process used with one embodiment of the present invention.

A package has been designed for this device that is specifically for the use in soil monitoring for the golf industry and agricultural applications. Many golf superintendents want to place sensors underneath the surface of putting greens, fairways and teeing boxes. However, they don't want to damage the surface of the green by digging large holes. The present invention has a preferred embodiment that has been designed into a package with a cross-section of less than 4 inches. This form factor can fit inside the hole left by a cup-cutter. The cup-cutter is a tool that is used to extract a 4.25" plug of dirt and grass from a putting green in order to place the golf hole and pin. This tool is used by all golf courses and creates a hole that can be easily filled by simply replacing the plug that was extracted. By designing the node so that it fits inside the hole left by a cup cutter, the node can be placed beneath the putting green very easily with tools that are already on-hand. A present invention device with an integrated soil condition sensor (or multiple ones) has been designed generally in accordance with FIG. 1 such that 3 metal pins exit the package parallel to the small cross-section so that the entire device with pins extending outward can be inserted into a hole in the turf created by a standard cup cutter as illustrated in the insertion process of FIG. 4. The device 34 is lowered into a hole in the turf so that the pins are parallel to the turf surface at the desired depth in the soil. The device and its protruding pins are then moved sideways to penetrate the undisturbed soil in the side of the hole. In this manner, the soil condition can be accurately measured at one or multiple depths (see for instance the device of FIG. 2) within one hole. After insertion the hole is repacked with soil and the turf cap plug is placed over the hole to restore the original turf surface.

The preferred embodiment of this device is constructed out of a rugged ABS plastic. The housing is molded ABS with a sealable lid so that it is robust against nearly all environmental conditions. The water tight lid must be robustly sealed to hermetically close the package so that no moisture is permitted to enter the package even under submerged conditions with large temperature swings over the day night cycles. Any protruding pins or wires must exit the package through sealed portals. The preferred embodiment uses O-rings held under pressure to seal between the package wall and the penetrating pins of the soil condition monitoring sensor.

Figure 7:
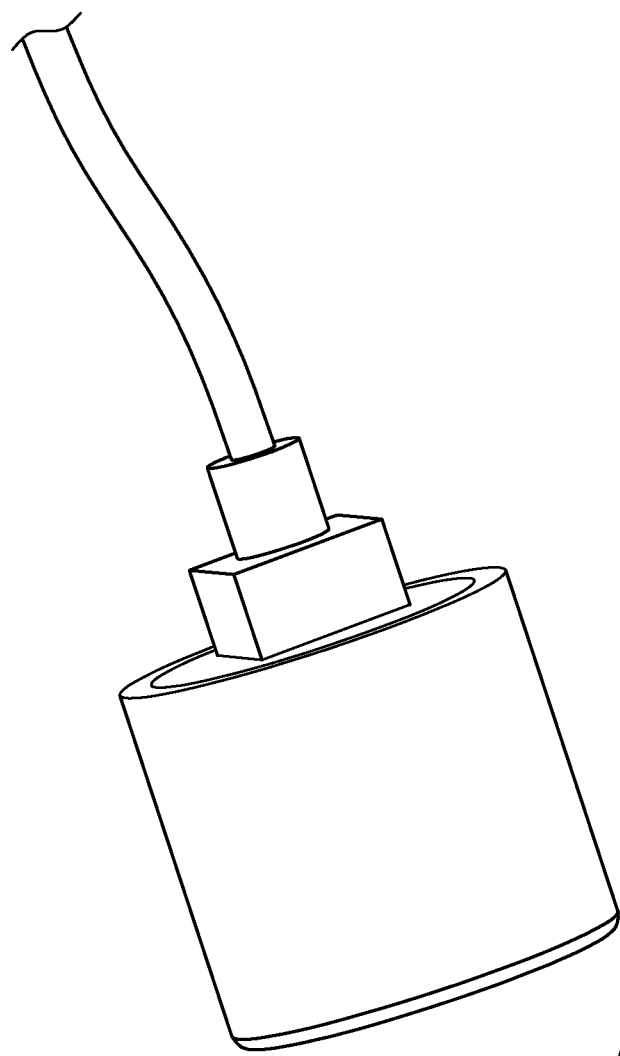
FIG. 7 is an illustration of still another embodiment of the present invention.

Three D-cell batteries are placed in the package and secured against a wall of the package to provide the source of Ground, 3V and 4.5V for the electronics. When fully sealed, there is a cavity above the batteries that is used to hold the electronics and circuit board necessary for the device operation. This cavity can also house an integrated antenna for the RF communication to and from the device. If external sensors are used, an Olflex Skintop connector part number S2109 with neoprene sealing ring may be used to form a seal with the wires exiting the device. This provides a seal capable of withstanding up to 70 PSI of pressure. The wires used to interface with external sensors may be direct-burial CAT-5 cable. This type of cable is filled with silicon so that no air or moisture can travel down the cable and into the sensor interface device. Additionally, this connector provides strain relief to prevent the wires from being pulled out of the device. As mentioned before, FIG. 5 provides an exploded drawing of the assembly of the sensor node and FIG. 6 provides a block diagram of the electronics. In the case of nodes that are connected to external sensors, an external connection is made through a bundle of wires that exits the device. This is depicted in FIG. 7.

Of importance to the design of the wireless sensor interface node is the electronics that are used to control the device and perform the wireless communication. The preferred embodiment devices are managed by a MSP430F149 microcontroller from Texas Instruments. The transceiver used is a CC1020 from Chipcon. This transceiver provides low power operation and fine frequency control that is well suited for this communication environment. During transmission, the RF output is amplified by a Maxim MAX2235 RF amplifier chip designed to amplify 900 MHz transmission. When transmitting at full power, the combination of the CC1020 and the MAX2235 produce up to a 1 W output signal. In order to boost receive sensitivity, a RF Micro Devices RF2361 Low Noise Amplifier (LNA) is used. The CC1020 and the MSP430F149 are capable of operating below 2.3 V while the Amplifier requires 2.7V-5V.

In order to current limit the drain on the battery from the RF amplifier operation, a 100 Ohm resistor is placed in series with the 4.5 V power supply leading to the Power Amplifier. To provide a current buffer, a 2 farad Aerogel ultra capacitor is used. This holds enough energy for a sustained three second transmission burst. Consequently the majority of the RF transmission energy comes from the capacitor, not directly from the batteries, with the batteries recharging the capacitor between transmissions.

Software

The hardware only represents a part of the total system. It must be accompanied by communication protocols and application software. The device runs an enhanced version of the TinyOS operating system. The device frequency hops at 150 hops per minute over 50 different channels evenly spaced across the 902-928 MHz band.

The device utilizes a unique protocol for establishing and maintaining precise hop synchronization. Upon initial boot-up, the device will transmit several search packets in order to quickly discover the current hop timing. A receiver node may pick up such packets and respond accordingly. Additionally, each receiver node will periodically send out sync announcements that can be received by a lost device. These sync announcements and replies to the sync requests contain information about the current channel and the current time value. Each device periodically checks the RF channel for the presence of a sync announcement. They check the channel for just a few milliseconds every second. If they detect that a sync announcement is eminent, they will leave their receiver on to receive the sync update. During a majority of the time, the transmitter node is powered down. Internally, it uses a low-power, 32 KHz, watch crystal to keep time. When it needs to transmit, it calculates what frequency the receiver has hopped to and transmits accordingly.

The software also handles interfacing with the sensors. In a preferred embodiment, each supported sensor has a separate device driver that interacts with the sensor. The device driver creates a 16 bit sensor output value that is placed into one of the node's 4 sensor reading buffers for transmission to the receiver. The software can be configured to have alarm points where emergency messages are transmitted if the sensor value is too high or low. Additionally, the software can control how often data is sampled and transmitted.

The TinyOS operating is used in the devices of the preferred embodiment in order for compatibility with the Mesh networking technologies. TinyOS provides open-source public domain implementations of advanced Mesh networking protocols and techniques. It also provides a framework for proprietary network extensions.

Thus while certain preferred embodiments of the present invention have been disclosed and described herein for purposes of illustration and not for purposes of limitation, it will be understood by those skilled in the art that various changes in form and detail may be made therein without departing from the spirit and scope of the invention.

What is claimed is:

1. A method for monitoring a soil moisture sensor, comprising:
    removing a portion of soil to create a hole in an area of turf;
    placing a first soil moisture sensor into said hole;
    moving said soil moisture sensor sideways towards a wall of said hole such that a first group of moisture sensor pins penetrate said wall at a first height and a second group of moisture sensor pins simultaneously penetrate said wall at a second height;
    packing soil around said soil moisture sensor;
    wirelessly transmitting sensor data from said first soil moisture sensor to one or more intermediate network nodes; wherein each of said one or more intermediate network nodes is an additional buried soil moisture sensor similar to said first soil moisture sensor; and
    further relaying said sensor data from said one or more intermediate network nodes to a collection point.

2. The method of claim 1, wherein said removing a portion of soil further comprises using a cup-cutter to create a 4.25 inch hole in said area of turf.

3. The method of claim 1, wherein said placing said soil moisture sensor into said hole further comprises lowering said soil moisture sensor into said hole such that said first group of moisture sensor pins and said second group of moisture sensor pins are parallel to a surface of said turf.

4. The method of claim 1, wherein said moving said soil moisture sensor further comprises moving said first group of moisture sensor pins and said second group of moisture sensor pins along a substantially parallel trajectory relative to a surface of said turf, into an undisturbed area of soil.

5. The method of claim 1, wherein said first group of moisture sensor pins have at least three pins and said second group of moisture sensor pins have at least three pins.

6. The method of claim 1, wherein said first group of moisture sensor pins are linearly arranged adjacent to a first end of said soil moisture sensor and said second group of moisture sensor pins are linearly arranged adjacent to a second end of said soil moisture sensor.

7. The method of claim 1, wherein said first group of moisture sensor pins have at least three pins and said second group of moisture sensor pins have at least three pins; and wherein said first group of moisture sensor pins are linearly adjacent to a first end of said soil moisture sensor and said second group of moisture sensor pins are linearly arranged adjacent to a second end of said soil moisture sensor.

8. A method for monitoring a soil moisture sensor, comprising:
    removing a portion of soil to create a cylindrical hole in an area of turf;
    placing a first soil moisture sensor into said hole;
    moving said first soil moisture sensor towards a wall of said hole such that a first group of moisture sensor electrodes penetrates said wall at a first depth and a second group of moisture sensor electrodes simultaneously penetrate said wall at a second depth;
    burying said portion of soil around said first soil moisture sensor;
    wirelessly transmitting sensor data from said first soil moisture sensor to one or more intermediate network nodes, wherein each of said one or more intermediate network nodes is an additional buried soil moisture sensor similar to said first soil moisture sensor; and
    further relaying said sensor data from said one or more intermediate network nodes to a collection point.

9. The method of claim 8, wherein said removing a portion of soil further comprises using a cup-cutter to create a 4.25" hole in said area of turf.

10. The method of claim 8, wherein said soil moisture sensor has a rectangular body.

11. The method of claim 8, wherein at least one side of said soil moisture sensor is rounded.

12. The method of claim 8, wherein said first group of moisture sensor electrodes have at least three electrodes and said second group of moisture sensor electrodes have at least three electrodes.

13. The method of claim 12, wherein said first group of moisture sensor electrodes are linearly arranged adjacent to a first end of said soil moisture sensor and said second group of moisture sensor electrodes are linearly arranged adjacent to a second end of said soil moisture sensor.

14. The method of claim 8, wherein said first group of moisture sensor electrodes are linearly arranged adjacent to a first end of said soil moisture sensor and said second group of moisture sensor electrodes are linearly arranged adjacent to a second end of said soil moisture sensor.

15. The method of claim 14, wherein said first group of moisture sensor electrodes and said second group of moisture sensor electrodes are rigidly fixed on a side of said sensor body.

16. The method of claim 8, wherein said moving said soil moisture sensor towards said wall further comprises moving a sensor body of said soil moisture sensor toward said wall of said hole such that said first group of moisture sensor electrodes and said second group of moisture sensor electrodes are inserted into an undisturbed area of soil along a substantially parallel trajectory relative to a surface of said turf.

17. A method for installing and monitoring a wireless soil moisture sensor, comprising:
- removing a portion of soil to create a hole in an area of turf;
- placing a first soil moisture sensor into said hole;
- moving said first soil moisture sensor towards a wall of said hole such that a first group of elongated soil electrodes move into an undisturbed region of soil at a first depth and a second group of elongated soil electrodes simultaneously move into said undisturbed region of soil at a second depth;
- wirelessly transmitting sensor data from said first soil moisture sensor to one or more buried soil moisture sensor similar to said first soil moisture sensor; and
- further relaying said sensor data from said one or more intermediate network nodes to a collection point.

18. The method of claim 17, wherein said first group of elongated soil electrodes are linearly arranged adjacent to a first end of said soil moisture sensor and said second group of elongated soil electrodes are linearly arranged adjacent to a second end of said soil moisture sensor.

19. The method of claim 18, wherein said first group of moisture sensor electrodes and said second group of moisture sensor electrodes are moved into said undisturbed region of soil along paths that are substantially parallel to a surface of said turf.

20. The method of claim 19, further comprising completely burying said soil moisture sensor with said portion of soil.

* * * * *